United States Patent
Zhang et al.

(10) Patent No.: US 6,403,844 B1
(45) Date of Patent: Jun. 11, 2002

(54) CONDENSED PHASE CATALYTIC HYDROGENATION OF LACTIC ACID TO PROPYLENE GLYCOL

(75) Inventors: Zhigang Zhang, East Lansing; Dennis J. Miller, Okemos; James E. Jackson, Haslett, all of MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/442,285

(22) Filed: Nov. 19, 1999

Related U.S. Application Data

(60) Provisional application No. 60/109,712, filed on Nov. 24, 1998.

(51) Int. Cl.$^7$ ............................................... C07C 27/00
(52) U.S. Cl. ........................ 568/864; 502/261; 502/326
(58) Field of Search ........................ 568/864; 502/261, 502/326

(56) References Cited

U.S. PATENT DOCUMENTS

| | | | |
|---|---|---|---|
| 2,607,807 A | * 8/1952 | Ford ........................... | 568/864 |
| 4,343,955 A | * 8/1982 | Oshima ....................... | 502/261 |
| 4,430,253 A | 2/1984 | Dubeck et al. | |
| 4,985,572 A | 1/1991 | Kitson et al. | |
| 5,149,680 A | 9/1992 | Kitson et al. | |
| 5,478,952 A | 12/1995 | Schwartz | |
| 5,536,879 A | 7/1996 | Antons et al. | |
| 5,600,028 A | 2/1997 | Gubitosa | |
| 5,731,479 A | 3/1998 | Antons | |
| 5,958,825 A | * 9/1999 | Wulff-Doring ............... | 568/864 |
| 6,248,924 B1 | * 6/2001 | Ruhl ........................... | 564/450 |

OTHER PUBLICATIONS

Szmant, H.H., Organic Building Blocks of the Chemical Industry, Wiley, New York, New York (1989) pp. 281–283.
Bowden and Adkins, J. Am. Chem. Soc. 56:689 (1934).
Adkins and Billica, J. Am. Chem. Soc. 70:3118 (1948).
Adkins and Billica, J. Am. Chem. Soc. 70:3121 (1948).
Broadbent et al., J. Org. Chem. 24:1847 (1959).
Brunauer et al, J. Am. Chem. Soc., 60:309 (1938).

* cited by examiner

Primary Examiner—Michael L. Shippen
(74) Attorney, Agent, or Firm—Ian C. McLeod

(57) ABSTRACT

The present invention provides a process for production of propylene glycol with high yield and selectivity in an aqueous reaction mixture of lactic acid and hydrogen with an essentially pure elemental ruthenium catalyst on an inert support at elevated pressure and temperature. In particular, the present invention provides a process wherein the catalyst is a ruthenium salt deposited on a microporous support, reduced to ruthenium on the support with hydrogen, and oxidized in the presence of oxygen to provide a ruthenium oxide surface on the surface of the ruthenium metal and wherein the catalyst is maintained in the surface oxidized state until it is reduced with hydrogen prior to the reaction process.

42 Claims, 8 Drawing Sheets

`US 6,403,844 B1`

CONDENSED PHASE CATALYTIC HYDROGENATION OF LACTIC ACID TO PROPYLENE GLYCOL

CROSS-REFERENCE TO RELATED APPLICATION

The application claims the benefit of U.S. Provisional Patent Application Ser. No. 60/109,712, filed Nov. 24, 1998.

STATEMENT REGARDING FEDERALLY SPONSORED RESEARCH OR DEVELOPMENT

This invention was sponsored by the United States Department of Agriculture under Contract Nos. 93-37500-9585 and 98-35504-6356 CSRS. The United States Government has certain rights in this invention.

BACKGROUND OF THE INVENTION (1) Field of the Invention

The present invention relates to a process for production of propylene glycol in high yield and selectivity in an aqueous reaction mixture of lactic acid and hydrogen with an essentially pure elemental ruthenium catalyst on an inert support at elevated pressure and temperature. In particular, the present invention relates to the process wherein the catalyst is a ruthenium salt deposited on a microporous support, reduced to ruthenium metal on the support with hydrogen, and oxidized with oxygen to provide a ruthenium oxide surface on the ruthenium metal and wherein the catalyst is maintained in the surface oxidized state until it is reduced with hydrogen prior to the reaction process.

(2) Description of Related Art

Propylene glycol is a nontoxic chemical used in polymer production; as a nontoxic antifreeze; in food, drinking, cosmetics, and pharmaceutical applications. In the United States, the production rate of propylene glycol is approaching one billion pounds per year, with growth projected at 5 to 7% per year.

Commercial production of propylene glycol is currently petroleum-based and involves the high pressure and high temperature hydrolysis of propylene oxide. Propylene oxide is manufactured by either the chlorhydrin process or the per-oxidation process (Szmant, H. H., Organic Building Blocks of the Chemical Industry, Wiley, New York, N.Y. pp. 281–283 (1989)). Making either propylene glycol precursor is a multi-step process that involves a variety of organic solvents and results in the formation of multiple byproducts. The selling price of propylene glycol using these petroleum-based precursors is about $0.60 to $0.65 per pound.

Alternative processes for producing propylene glycol have been reported. For example, the hydrogenation of organic esters to alcohols and glycols was reported by Adkins and co-workers who were able to achieve 80% yields of propylene glycol from methyl lactate over copper/chromium oxide and Raney nickel catalysts at 150° to 250° C. and extremely high hydrogen pressures of about 20 to 30 MPa (2,900 to 4,350 PSIG) (Bowden and Adkins, J. Am. Chem. Soc. 56: 689 (1934); Adkins and Billica, J. Am. Chem. Soc. 70: 3118 (1948); Adkins and Billica, J. Am. Chem Soc. 70: 3121 (1948)). In addition to high pressures, high catalyst loadings were necessary as well to achieve these relatively high yields. Broadbent et al. (J. Org. Chem. 24: 1847 (1959)) was able to obtain propylene glycol yields as high as 80% from ethyl lactate at 150° C. over rhenium black catalysts, but at very high hydrogen pressures of about 25 MPa (3,626 PSIG). More recently, U.S. Pat. No. 5,731,479 to Antons discloses a process for preparing optically active alcohols from optically active carboxylic acids with hydrogen in the presence of ruthenium catalysts. An example is provided for the conversion of optically active L-(+)-lactic acid to L-(+)-propane-1,2-diol. The yields obtained were about 88% over bulk ruthenium powder, and 74% over ruthenium supported on carbon. To achieve efficient conversion of an optically active carboxylic acid to its corresponding optically active alcohol, the process is performed at a relatively high pressure (10 to 20 MPa) and the reaction is allowed to proceed to completion.

While the aforementioned relate to the conversion of lactic acid and derivatives to propylene glycol, there are several U.S. Patents related to the aforementioned which disclose various mixed bed catalysts and processes for their use in hydrogenation reactions for converting organic acid esters to their alcohols.

U.S. Pat. Nos. 4,985,572 and 5,149,680 to Kitson et al discloses a process for catalyzed hydrogenation of carboxylic acids and their anhydrides to produce the corresponding alcohol and/or carboxylic acid ester and catalysts for achieving the conversion. The process is particularly applicable to the hydrogenation of dicarboxylic acids and their anhydrides using catalysts that comprise an alloy of a noble metal from Group VIII of the Periodic Table of Elements and at least one metal capable of alloying with the Group VIII noble metal.

U.S. Pat. No. 5,478,952 to Schwartz discloses improved hydrogenation catalysts consisting essentially of highly dispersed, reduced ruthenium and rhenium on carbon supports. Specifically, the catalyst relates to the production of tetrahydrofuran, gamma-butyrolactone, 1,4-butanediol and the like from a hydrogenatable precursor such as maleic acid, succinic acid in an aqueous solution in the presence of hydrogen and one of the above catalyst.

Finally, U.S. Pat. No. 5,536,879 to Antons et al. discloses a hydrogenation process which uses ruthenium catalysts to prepare optically active amino alcohols from optically active amino acids. The process is performed at relatively high pressures to achieve efficient conversion of the amino acid to its corresponding alcohol.

The catalysts used in the above related patents can be adapted to convert lactic acid to propylene glycol. However, the disclosed hydrogenation reactions generally have inadequate yields and selectivities to propylene glycol. Inadequate selectivity results in the production of unwanted alkanes, such as methane and ethane, by side reactions. Because these byproducts reduce overall yield and contaminate the final product, the byproducts increase the overall costs associated with producing propylene glycol from lactic acid. Therefore, commercial production of propylene glycol remains dependent on petroleum-based routes for its synthesis.

Thus, there remains a desire to provide a low-cost process for producing propylene glycol from renewable resources. In particular, it would be desirable that the process enable the bulk production of propylene glycol in a process that can be performed under relatively mild conditions which results in high yields and selectivity for propylene glycol.

SUMMARY OF THE INVENTION

The present invention provides a process for the low-cost, bulk production of propylene glycol from lactic acid. The process produces high yields of propylene glycol from "crude or unrefined" lactic acid under reaction conditions with high selectivity and, therefore, low byproduct formation. Thus, the present invention provides a process for the production of propylene glycol, which comprises: reacting a reaction mixture of lactic acid and hydrogen in water with a ruthenium catalyst on an inert support with a BET surface area between about 1 to 1,000 $m^2$ per gram at a hydrogen pressure between about 3.4 to 16.5 MPa (500 to 2,400 PSIG) and a temperature between about 500 to 200° C., more preferably between 1000 and 170° C.; and removing the propylene glycol from the reaction mixture.

The present invention also provides a composition which comprises an essentially pure elemental ruthenium on an inert microporous support, wherein the ruthenium is deposited on the support by drying a water solution of the ruthenium salt on the support, reducing the salt to the elemental ruthenium on the support with hydrogen, and then reacting the ruthenium on the support with oxygen to provide oxide of the ruthenium on surfaces of the ruthenium. Preferably, the ruthenium is deposited on an inert microporous support selected from the group consisting of alumina, titania, silica, alumina silicate, and microporous carbon.

The process of the present invention is preferably conducted at hydrogen pressures of 3.4 to 8.3 MPa (500 to 1,200 PSIG) in a continuous or batch process. When the process is a batch process, the reaction mixture is in a closed vessel provided with a stirrer which agitates the reaction mixture. When the process is a continuous process, the continuous process is a preferably a fixed bed reactor and the reaction mixture is trickled through a bed of the catalyst. Further, in the continuous process the gas flow can either be up or down. In a preferred embodiment, the hydrogen gas mixture is passed upward through the bed and the aqueous reaction mixture flows downward. In the continuous process it is preferable that the reaction mixture has a space velocity of between about 0.5 and 5 grams of lactic acid per gram of the catalyst per hour. In either the batch or continuous process, the reactor temperatures are preferably between about 500 and 200° C., and more preferably between 100° and 170° C., for maximum results. Finally, to reduce the formation of reaction byproducts, the reaction mixture can further comprise sulfur added either to the liquid or gas phase.

The present invention further provides that the lactic acid can be provided to the reaction as a fermentate produced by a microorganism or other crude or unrefined preparation. In general, when the lactic acid is produced be a microorganism, the lactic acid may be converted to its salt during processing of the fermentate which can then be acidulated. Therefore, when the lactic acid is provided in a solution as its salt or a partially acidulated salt, this "crude or unrefined" reaction mixture may further comprise $H_2SO_4$ or other acid. Preferably, the $H_2SO_4$ is added to the lactic salt solution to provide a 1 to 1 molar ratio of lactate salt to acid equivalent and the anion, other than lactate is substantially removed. In general, the lactic acid so produced is provided at a concentration between about 5% to 90% by weight of the reaction mixture.

Thus, in a preferred embodiment, the present invention provides a process for preparation of propylene glycol comprising: (a) providing a ruthenium metal catalyst prepared by reacting hydrogen gas with a ruthenium salt deposited and dried on an inert microporous support having a BET surface area between about 1 and 1,000 $m^2$ per gram; (b) drying the catalyst in an oxygen containing atmosphere so as to provide oxide of the ruthenium on surfaces of the ruthenium; (c) introducing the dried catalyst into a reaction vessel; (d) reacting the catalyst with the oxide on the surface with hydrogen in the vessel; (e) reacting in the vessel at elevated pressures and at elevated temperatures, a reaction mixture of a lactic acid in water in the presence of the catalyst, wherein the temperature is between about 50° to 200° C., preferably between 100° and 170° C. and the hydrogen pressure is between about 3.4 to 16.5 MPa (500 to 2,400 PSIG) to produce the propylene glycol in the reaction mixture; and (f) recovering the propylene glycol from the reaction mixture. In a preferred embodiment, the ruthenium is deposited on a support selected from the group consisting of alumina, titania, silica, alumina silicate, and microporous carbon. To reduce the formation of reaction byproducts, the reaction mixture can further comprise sulfur.

In the foregoing processes of the present invention, the propylene glycol is recovered in a yield of at least 80%, preferably in excess of 90%, and a selectivity to propylene glycol of at least 80%, preferably in excess of 90%.

The present invention further provides a composition which comprises an essentially pure elemental ruthenium on an inert microporous support, wherein the ruthenium is deposited on the support by drying a water solution of ruthenium salt on the support, reducing the salt to elemental ruthenium on the support with hydrogen, and passivating the composition in an oxygen containing atmosphere so as to provide an oxide of the ruthenium on surfaces of the ruthenium. Preferably, the inert microporous support is selected from the group consisting of alumina, titania, silica, alumina silicate, and microporous carbon. In a preferred embodiment, the inert microporous support has a BET surface area between about 1 to 1,000 $m^2$ per gram, more preferably between about 100 to 1,000 $m^2$ per gram. Preferably, drying the ruthenium salt on the catalyst is at about 25° C. for about 5 hours and then under a vacuum of about 30 inches of mercury at about 100° C. for 12 hours. Preferably, reducing the ruthenium salt to elemental ruthenium comprises the steps of (a) heating the catalyst from 25° C. to 400° C. at a rate of about 0.5° C. per minute under a flow of a gas consisting of 10 volume percent of hydrogen in helium at a rate of about 30 ml per minute; (b) maintaining the catalyst at 400° C. and changing the gas to pure hydrogen; (c) reducing the catalyst in the pure hydrogen for about 16 hours; and cooling the catalyst under a helium flow to room temperature. Preferably, passivating the catalyst by placing the reduced catalyst in a stream of about 1 to 10, preferably between 1 and 3, volume percent of oxygen in argon or other inert gas at room temperature for about 1 hour. For using the composition for the conversion of lactic acid to propylene glycol, it is preferable that the ruthenium is reduced in a reaction vessel with hydrogen prior to contact with a reaction mixture.

Therefore, it is an object of the present invention to provide a process for producing propylene glycol in a reaction mixture using a substrate that is derived from renewable resources. In particular, a process which uses lactic acid which can be produced inexpensively in fermentation cultures.

It is also an object of the present invention to provide a process for producing propylene glycol from lactic acid which has high selectivity and yield.

It is further an object of the present invention to provide a composition that is a catalyst for the conversion of lactic acid to propylene glycol that effects the conversion at high yields and selectivities.

DESCRIPTION OF PREFERRED EMBODIMENTS

Figure 1:
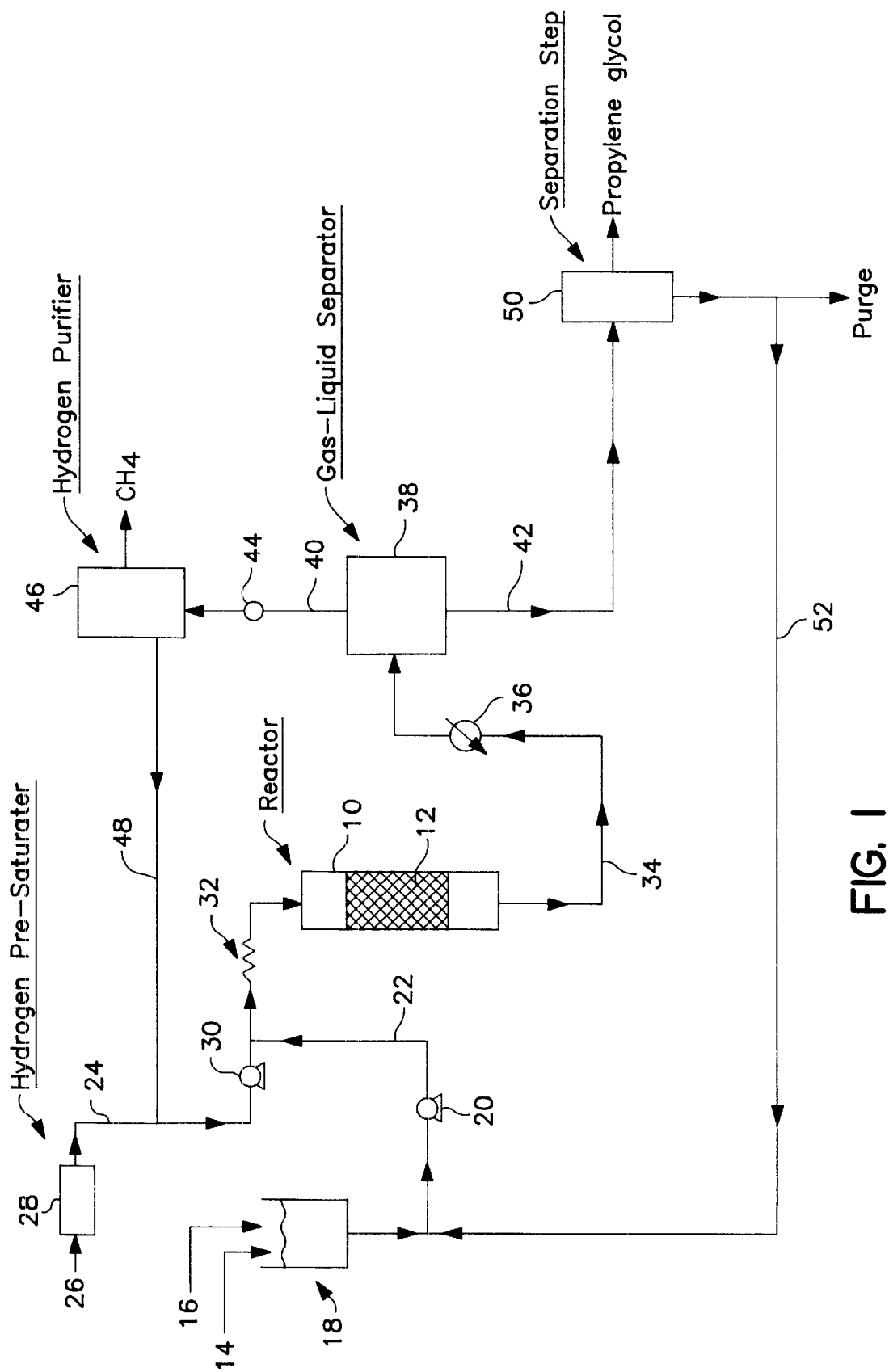
FIG. 1 is a flow diagram for a process for converting lactic acid to propylene glycol in a continuous trickle-bed reactor.

As used herein, the term "MPa" refers to mega-Pascal which is the SI unit of measure for pressure or stress. 1 MPa is equivalent to 1 PSIG$\times 6895.757/10^6$; or, 1 bar$\times 100,000/10^6$ or 1 atmosphere (atm)$\times 101,325/10^6$; or, 1 inches of mercury$\times 3386.388/10^6$.

BET surface area of the inert supports was calculated according to the method of Brunauer, Emmett, and Teller (BET) disclosed in J. Am. Chem. Soc., 60: 309 (1938).

The present invention provides an improved process for the conversion of lactic acid in a feedstock to propylene glycol with high selectivity and yield. A key component of the process is a catalyst comprising ruthenium on an inert support which includes carbon, alpha-alumina, gamma-alumina, alumina siliconate, silica, or titania.

In a preferred embodiment, the catalyst comprises ruthenium metal deposited on an inert support such as carbon or alumina which is preferably a microporous support that has a BET surface area between about 1 to 1,000 m² per gram, preferably between about 100 to 1,000 m² per gram, so as to facilitate high selectivity of the reaction to propylene glycol. In a preferred embodiment, the support is a microporous carbon support. The ruthenium metal is deposited on the support by mixing an aqueous solution of a precursor ruthenium salt in an amount just sufficient to fill the pore volume of the support. Preferably, the ruthenium salt is ruthenium chloride and the ruthenium loading is between about 4 to 5 wt %. After depositing the ruthenium in and/or on the support, the ruthenium salt impregnated support is dried. In particular, the catalyst is dried at room temperature for between about 5 to 16 hours, preferably about 5 hours, and then under a vacuum at between about 50° C. to 100° C. for between about 4 to 12 hours, preferably 100° C. for 12 hours. Preferably, the vacuum is about 30 inches of mercury. Then the ruthenium salt is reduced by heating at an elevated temperature under hydrogen. In particular, the catalyst is heated from 25° C. to 400° C. under a hydrogen containing gas at a flow rate about 0.50° C. per minute wherein the gas is between about pure hydrogen to 10 volume percent hydrogen in helium, preferably 10 volume percent hydrogen in helium. When 400° C. has been reached, the gas is switched to pure hydrogen and the reduction is continued for 8 to 16 hours, preferably 16 hours. After reduction, the catalyst is cooled to room temperature and passivated in an oxygen containing atmosphere which coats the surface of the ruthenium to provide an oxide of the ruthenium on the surface of the ruthenium. In particular, the catalyst is cooled under an argon, helium or other inert gas flow, preferably helium, and then passivated in a stream of oxygen between about 1 and 10, preferably between about 1 to 3 volume percent of oxygen in argon. The oxidized metal surface enables the catalyst to be maintained without using elaborate storage conditions. Prior to using the passivated catalyst in the improved process reaction, the catalyst is reduced with hydrogen. After reducing the catalyst, the lactic acid feedstock is added to the catalyst and the reaction is performed under pressure in a hydrogen atmosphere and at an elevated temperature. The catalyst which is prepared in this manner is able to perform at high efficacy for a significantly longer period of time than prior art catalysts. In particular, the catalyst facilitates the efficient conversion of lactic acid to propylene glycol at temperatures and hydrogen pressures that are significantly milder than conditions reported in the prior art. For example, the process of the present invention enables the efficient conversion of lactic acid to propylene glycol at 150° C. and hydrogen pressures as low as 3.3 MPa (479 PSIG).

Examples of catalysts that were prepared according to the present invention are shown in Table 1. Of the prepared catalysts, the following catalysts are preferred in the process of the present invention which is a catalyst that consists of ruthenium metal on a microporous support with a ruthenium metal loading of between about 4 to 5% is preferred. An example of a ruthenium on microporous support catalyst which is preferred is CG6M-F (Table 1, run number 3) wherein the support is a 110+200 carbon support with a BET surface area of 728 m² per gram (available from Cameron-Yakima, Inc., Yakima, Washington). The ruthenium metal loading is about 5.0 wt % and is applied to the support as an aqueous solution of ruthenium chloride hydrate with a dispersion of about 13%.

Another example of a ruthenium on microporous support catalyst that is preferred is SG6-D (Table 1, run number 5) wherein the support is a 100 mesh microporous support with a BET surface area of 777 m² per gram (available from Cameron-Yakima, Inc.). The ruthenium metal loading is about 4.4 wt % and is applied as an aqueous solution of ruthenium chloride hydrate with a dispersion of about 10%.

TABLE 1

| | | Support | | | | |
| --- | --- | --- | --- | --- | --- | --- |
| Run | Catalyst | Name | BET (m²/gram) | Precursor | Dispersion | Loading |
| 1 | CG5P-G | Cameron-Yakima, Inc. CG5P-200 mesh | 648 | Aldrich ruthenium (III) chloride hydrate (aq) | 6% | 5.0% |

TABLE 1-continued

| Run | Catalyst | Support Name | BET (m²/gram) | Precursor | Dispersion | Loading |
|---|---|---|---|---|---|---|
| 2 | CG5P-H | Cameron-Yakima, Inc. CG5P-200 Mesh | 648 | Aldrich ruthenium (III) chloride hydrate (EtOH) | 3% | 5.0% |
| 3 | CG6M-F | Cameron-Yakima, Inc. macroporous-100 +200 | 728 | Aldrich ruthenium (III) chloride hydrate (aq) | 13% | 5.0% |
| 4 | SA135-C | Aldrich silica-alumina grade 135, −100 mesh | 440 | Aldrich ruthenium (III) chloride hydrate (aq) | 14% | 5% |
| 5 | SG6-D | Cameron-Yakima, Inc. microporous 100 mesh | 777 | Aldrich ruthenium (III) chloride hydrate (aq) | 10% | 4.4% |
| 6 | CG5P-NO1-I | Cameron-Yakima, Inc. CG5P-200 mesh | 648 | Alfa ruthenium nitrosyl nitrate hydrate (aq) | 38% | 5% |
| 7 | CG5P-A | Cameron-Yakima, Inc. CGSP (20*50 mesh) | 648 | Aldrich ruthenium (III) chloride hydrate (aq) | 10% | 5.4% |
| 8 | AL100-B | Aldrich alpha aluminum oxide (−100 +200 mesh) | 0.24 | Aldrich ruthenium (III) chloride hydrate (aq) | 0% | 5% |
| 9 | ALg-E | Alfa gamma aluminum size +100 mesh | 45 | Aldrich ruthenium (III) chloride hydrate (aq) | 13.5% | 4.7% |
| 10 | TiP25-C19-J | Degussa P25 Titania-200 mesh | 49 | Aldrich ruthenium (III) chloride hydrate (aq) | 18% | 5% |

A further example of a ruthenium on microporous support catalyst that is preferred is CG5P-NO1-I (Table 1, run number 6) wherein the support is a microporous CG5P-200 mesh support with a BET surface area of 648 m² per gram (available from Cameron-Yakima, Inc.). The ruthenium metal loading is about 5.0 wt % and is applied as an aqueous solution of ruthenium nitrosyl nitrate hydrate with a dispersion of about 38%.

An example further still of a ruthenium on a microporous support catalyst that is preferred is CG5P-A (Table 1, run number 7) wherein the support is a microporous CG5P 20*50 mesh support with a BET surface area of 648 m² per gram (available from Cameron-Yakima, Inc.). The ruthenium metal loading is about 5.4 wt % and is applied as an aqueous solution of ruthenium chloride hydrate with a dispersion of about 10%.

A catalyst which consists of a ruthenium metal on a silica-alumina support with a ruthenium metal loading of between about 4 to 5% is also preferred. An example is SA135-C (Table 1, run number 4) wherein the ruthenium metal is on a Silica-alumina grade 135, −100 mesh support with a BET surface area of 440 m² per gram (available from Aldrich Chemical Company, Milwaukee, Wis.). The ruthenium metal is applied to the support as an aqueous solution of ruthenium chloride hydrate with a dispersion of about 14%.

A catalyst which consists of a ruthenium metal on titania support with a ruthenium metal loading of between about 4 to 5% is also preferred. An example is TiP25-C19-J (Table 1, run number 8) wherein the ruthenium metal is on a titania 200 mesh support with a BET surface area of 49 m² per gram (available from Degussa, Inc.). The ruthenium metal is applied to the support as an aqueous solution of ruthenium chloride hydrate.

Further still, a catalyst which consists of a ruthenium metal on a gamma aluminum oxide support with a ruthenium metal loading of between about 4 to 5% is also preferred. An example is ALg-E (Table 1, run number 9) wherein the ruthenium metal is on a gamma aluminum oxide +200 mesh support with a BET surface area of 45 m² per gram (available from Johnson-Matthey Chemicals, Inc.). The ruthenium metal is applied to the support as an aqueous solution of ruthenium chloride hydrate with a dispersion of about 13.5%.

An important aspect of the present invention is that "unrefined" or crude lactic acid preparations can be efficiently converted to propylene glycol in the foregoing process. "Unrefined" lactic acid as used herein can contain more than 100 parts per million alkali metal, alkaline earth metal, or ammonium salts of lactic acid. Therefore, "unrefined" lactic acid includes bacterial fermentates and other crude or impure preparations of lactic acid. The conversion processes of the prior art require pure preparations of lactic acid or its esters as the substrate for conversion to propylene glycol whereas the present invention can efficiently convert the lactic acid in crude preparations to propylene glycol. This is an important improvement over the processes of the prior art. Thus, in the present invention, the "unrefined" or impure lactic acid is either a fermentate or lactic acid containing lactate salts. Impure lactic acid preferably contains 50 to 100% lactic acid.

In general, "unrefined" lactic acid is produced by microorganisms such as the homolactic microorganisms *Lactobacillus delbruceckii, L. bulgarcius,* and *L. leichmanii* in a fermentor. The microorganisms produce lactic acid which is converted to its salt during the fermentation process, through addition of a base in order to control pH. Therefore, in fermentation, lactic acid is produced as lactate salt, which may be partially acidulated to produce a lactic acid and lactate salt mixture. This mixture can be treated by the process of the present invention which provides an economic source of lactic acid. Residual lactate can be, further acidified and/or can be recycled into the crude broth. Lactate salt could be in the form as a fermentate, alkali metal, and alkali earth, or ammonium lactate. The lactic fermentate can be partially or fully acidulated. The conversion of lactate to its acid can be achieved by addition of sulfuric or other acid to the fermentate.

Since producing lactic acid by fermentation is less expensive than producing lactic acid by chemical synthesis, it would be desirable to use fermentation methods to produce the lactic acid for the hydrogenolysis reaction. Furthermore, the fermentation process allows renewable resources to be used to produce propylene glycol. The following materials are renewable resources which among other renewable resources can be used in lactic acid fermentation: products containing starch (q.v.), i.e., corn starch, potato starch, or rice starch; whey; dextrose; corn sugar; cane sugar, beet sugar, or molasses of beet sugar; and sulfate lyes. Ammonium salts or other nutrient sources are used as nitrogen sources. The fermentation is performed according to methods well known in the art to produce lactic acid.

After fermentation, biomass, magnesium hydroxide, limestone, and other nutrients and ingredients that may have been in the water are removed by filtration. Optionally, the filtrate is concentrated by evaporation, then the filtrate is acidified with sulfuric acid, usually at a hydrogen to lactate molar ratio of 1 to 1 to regenerate the lactic acid and precipitate the calcium as calcium sulfate. The resulting filtrate consists of about 10% crude lactic acid which may be concentrated to greater than 50%. It is this "unrefined" lactic acid which can be used in the process of the present invention to make propylene glycol. In a preferred process for the conversion of "unrefined" lactic acid, the reaction is performed with a 5% ruthenium catalyst at 150° C. and 14.5 MPa hydrogen pressure.

Alternatively, the "unrefined" lactic acid can be further purified in a refining process well known to those skilled in the art which includes treating the "unrefined" lactic acid solution with activated vegetable carbon to remove organic impurities, treating the solution with ferrocyanide to remove heavy metals, and finally filtrating the solution to remove impurities that have coagulated during purification. The solution may also be passed through ion-exchange resins to remove the last traces of contamination. This further purified lactic acid may be used as the substrate in the present invention to make propylene glycol.

The present invention further comprises the conversion of lactic acid to propylene glycol as shown above except that the feedstock mixture further comprises a small quantity of sulfur. In U.S. Pat. No. 5,600,028 to Gubitosa and U.S. Pat. No. 4,430,253 to Dubeck, which are hereby incorporated herein by reference, in the hydrogenolysis of sugar over ruthenium catalysts it was shown that the addition of small quantities of sulfur partially poisoned the ruthenium catalyst. While the poisoned catalyst had a lowered conversion rate, the formation of methane and ethane byproducts in the reaction was essentially eliminated. Therefore, in an embodiment of the process of the present invention that has reduced formation of methane and ethane byproducts, the lactic acid feedstock further comprises sulfur which can enhance the selectivity of the reaction to propylene glycol by reducing lactic acid conversion to the hydrocarbon byproducts methane and ethane. The decrease in catalyst activity stemming from the addition of the sulfur can be compensated for by preforming the process at slightly higher reaction temperatures or longer space velocities.

FIG. 1 shows a process for the conversion of lactic acid to propylene glycol in a continuous flow reactor. The process comprises a reactor 10 which is a three-phase reactor commonly run as a trickle bed that contains a fixed bed of catalyst 12. Lactic acid is provided as a water solution at 14. When the lactate is "unrefined" lactate produced by a microorganism in a fermentor, the "unrefined" lactate is mixed with $H_2SO_4$ provided at 16 to produce preferably a 1 to 1 molar ratio of lactic acid to $H^+$ solution. The resulting solution mixed at 18 is pressurized at 20 and the solution feedstream 22 mixed with fresh hydrogen stream 24 before being fed to the reactor 10. Before the hydrogen stream 24 is mixed with the solution feedstream 22, hydrogen at 26 is optionally passed through a pre-saturator 28 and the resulting hydrogen stream 24 is pressured by compressor 30. Optionally, the feedstock stream 22 and hydrogen stream 24 are heated in a preheater 32 to the desired temperature and passed downwardly or upwardly through the bed in intimate contact with the catalyst 12. Thus, the gas flow can be cocurrent or countercurrent to the feedstock flow.

Thus, in a typical process of the present invention, the passivated catalyst 12 is introduced into the reactor 10 and re-reduced with hydrogen stream 24 without feedstream 22 for about 60 minutes under pressure of about 1.7 MPa (250 PSIG). A volume of hydrogen (STP) equal to 50 times the volume of catalyst is used to ensure complete catalyst reduction. Preferably, the passivated catalyst is 5% ruthenium on an inert support such as alumina, titania, silica, aluminosilicate or microporous carbon. After re-reducing the catalyst 12, the reactor 10 is allowed to cool below 150° C. and vented to low pressure. Then, feedstream 22 containing the lactic acid feedstock solution is introduced in mixture with hydrogen stream 24 into the reactor 10 without opening the reactor. The feedstream rate is adjusted to give a weight hourly space velocity of about 0.5 gram to 5.0 gram lactic acid per gram catalyst per hour. The hydrogen to lactic acid feed molar ratio ranges from about 1.4 to 1 to 8.7 to 1, with a preferred value of about 4.2 to 1. The reaction is carried out at a temperature between 50° C. to 20° C., preferably between about 700 to 150° C., and the hydrogen pressure is increased to a desired value, usually 3.4 to 16.5 MPa (500 PSIG to 2,400 PSIG), and preferably between 3.4 MPa to 10.3 MPa (500 to 1,500 PSIG).

After the reaction, the reactor effluent stream 34 is cooled to below 40° C. in a heat exchanger 36 against a suitable fluid such as water, and/or other process stream that requires heating, e.g., a process hydrogen stream. The cooled effluent stream is passed through a gas-liquid separator 38, wherein the fluid is separated into an overhead gas stream 40 and a bottom liquid stream 42. The overhead stream 40 contains mainly hydrogen and some methane, and is pressure reduced at 44 and passed to hydrogen purification unit 46. Here the gas is purified to about 90 vol % hydrogen and recycled as stream 48 through compressor 30 to reactor 10.

In a typical separation for recovering propylene glycol (not shown), the bottom liquid stream 42 is preheated and passed to a low pressure separator from which overhead water vapor is withdrawn. Then, the liquid product is passed through a water distillation column which removes water from the liquid product. Finally, the liquid product from the water column is fed to a propylene glycol recovery column wherein the propylene glycol is recovered.

In some cases the bottom liquid stream 42 may contain monohydroxide alcohols, particularly when the starting material consists of starting polyols produced in sugar conversion reactions. Therefore, in an optional step, the bottom liquid stream 42 is passed to an alcohol separation column at about atmosphere pressure wherein monohydroxide alcohols are removed, if present, before being passed to the low pressure separator. Also, in some cases the bottom liquid stream 42 may need to be demineralized, particularly when the feedstock is a fermentate wherein the lactate salt has been converted to lactic acid with sulfuric acid. Therefore, in an optional step, the bottom liquid stream 42 is demineralized in a demineralizer containing cationic resins to remove ions from the bottom liquid stream 42 before being passed to the low pressure separator or alcohol separation column.

Figure 2:
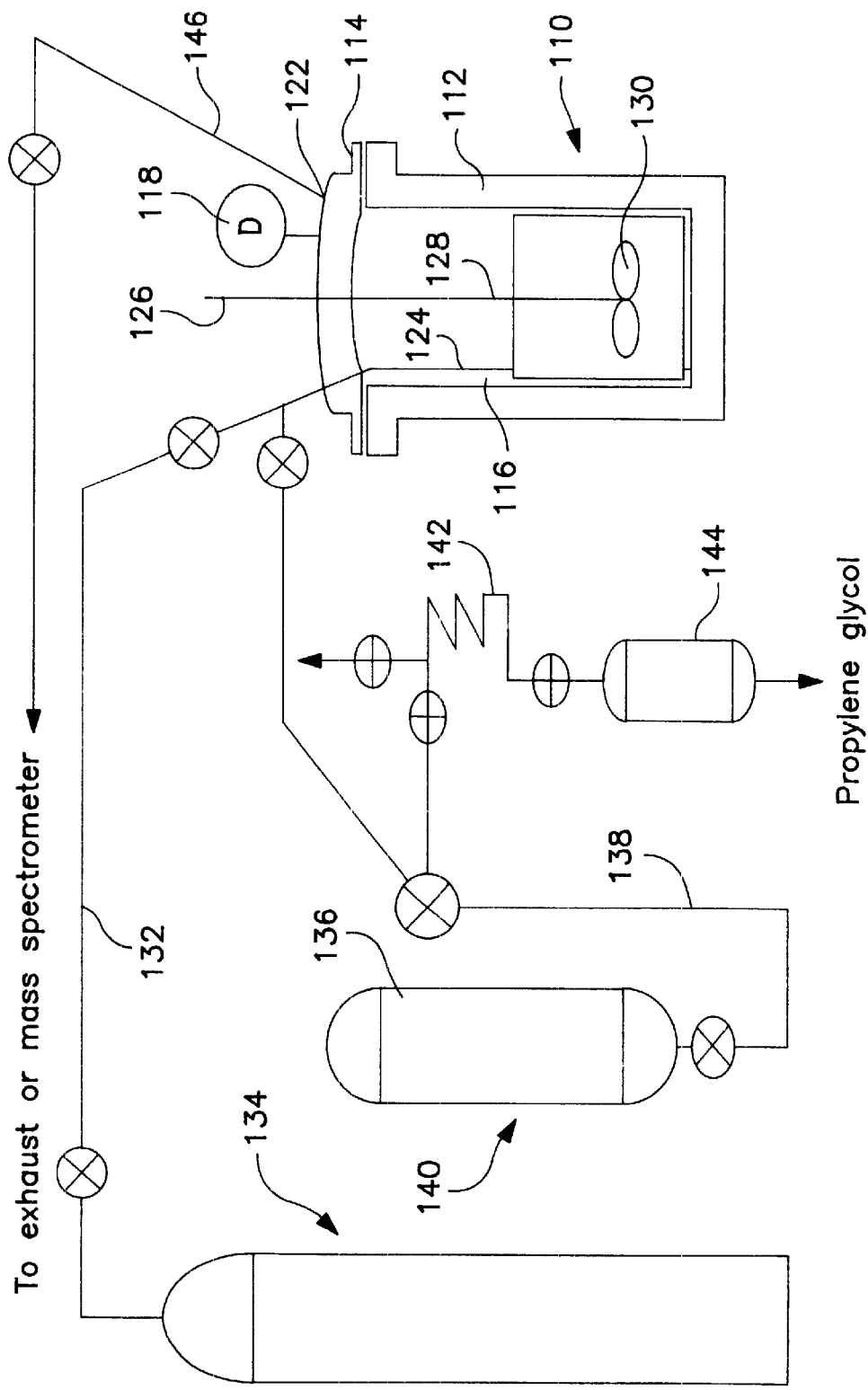
FIG. 2 is a flow diagram for a process for converting lactic acid to propylene glycol in a batch reactor.

The process of the present invention is also efficient when performed in a batch reactor. A typical batch reaction setup is shown in FIG. 2. The batch reactor 110 consists of a vessel 112 and a lid 114 and a quartz liner 116 to prevent corrosion of the metal surfaces of the reactor 110. The reactor 110 is controlled by a controller 118 which provides adjustable stirring speed for speeds preferably between about 10 and 1,000 rpm, electric heater power, and automatic temperature control to maintain a temperature preferably between about 80° C. and 170° C. The reactor is further equipped with a valve 120 for charging gas into the reactor 110, a gas release valve 122 for releasing pressure, a dip tube 124 connected to valve 122 for adding or withdrawing sample from the reactor 110 under pressure, a safety rupture disk for providing over pressure protection (not shown), a thermocouple for temperature measurements (not shown), and a stirrer 126 consisting of stirring shaft 128 with a gas entrainment propeller 130. The stirrer 126 is regulated by a stirrer drive system which is a packless magnetic drive.

The hydrogen is supplied to the reactor through gas stream 132 from tank 134. The feedstock solution 136 is supplied to the reactor 110 through feedstock stream 138 from vessel 140. Reaction samples are removed through sample stream 142 from the reactor 110 for testing in the sampling apparatus 144.

In a typical batch reaction, the desired amount of passivated catalyst is loaded into the reactor 110. In general, between about 0.1 to 5.0 gram of catalyst is loaded for every 100 grams of feedstock solution, preferably between about 0.5 to 2.5 gram per 100 ml. Then the reactor 110 is sealed and purged three times with hydrogen to 3.3 MPa (479 MPa), and then filled with hydrogen to 2.0 MPa (290 PSIG). The reactor 110 is then heated to 150° C., the stirrer 126 is set at 50 rpm, and held at that temperature and hydrogen pressure for one-half hour to complete the reduction of the catalyst. Meanwhile, the feedstock vessel 140, which is connected to the reactor by a feedstream 138, is purged with hydrogen twice, and then filled with the desired amount of lactic acid solution, sealed and pressurized.

After the catalyst has been re-reduced, the reactor 110 is depressurized and the feedstock is introduced into the reactor 110 via feedstream 138. The reactor 110 is pressurized to between about 3.4 to 16.5 MPa (500 and 2,400 PSIG), preferably between about 3.4 MPa to 10.3 MPa (500 PSIG to 1,500 PSIG), and changing the reactor set point, if required. The typical feedstream charge to the reactor is 100 ml of lactic acid feedstock. The stirring speed is increased to 1,000 rpm. During the reaction, liquid samples can be removed and analyzed by high performance liquid chromatography (HPLC), and gas samples can be analyzed by mass spectrometry. The typical reaction can last from 2 to 8 hours, with 4 to 6 hours being the most common. After the reaction, the valve 120 is closed and the reactor 110 is allowed to cool to below 40° C. Then the reactor 110 is depressurized and purged of hydrogen via exhaust stream 146. Finally, the reaction solution is removed and the propylene glycol is recovered by a propylene glycol recovery column as shown previously.

The following examples are intended to promote a further understanding of the present invention.

EXAMPLE 1

The catalysts having the properties of the catalysts shown in Table 1 were prepared according as follows.

The carbon support was first tested to determine its pore volume by adding water to incipient wetness, and then dried for 5 hours at 100° C. in 30 Hg vacuum. An amount of ruthenium (III) chloride hydrate ($RuCl_3 \cdot 6H_2O$, available from Aldrich Chemical Company) sufficient to provide a 5 wt % loading of Ruthenium metal was then added to a quantity of water just sufficient to fill the pore volume. Then the carbon support was added to this solution and the mixture stirred. The impregnated carbon was then dried at 25° C. for 16 hours and then 50° C. for 4 hours under vacuum. Reduction was accomplished by heating under 100% $H_2$ in a tube furnace at 0.5° C. per minute to 400° C. and then holding at 400° C. for 8 hours. The catalyst was then cooled in pure argon to room temperature and then passivated in a 2% oxygen in argon mixture for one hour. Other catalysts were prepared as shown above with the exception that they were reduced at different gas compositions ($H_2$/He mixtures), at different temperatures, and for different reduction time lengths; however, the above method is preferred.

To determine the dispersion of ruthenium on the support, hydrogen chemisorption was used. Measured dispersions ranged from 1% to 50%.

EXAMPLE 2

This example was performed to determine the efficacy of several of the catalysts that were prepared in Example 1. The prepared catalysts that were evaluated in this example were 5% ruthenium on carbon (Ru/C) (CG6M-F), 5% Ru/C (CG-5P-G), and 5% Ru/C (CG5P-H). The batch reactor process was as follows.

The lactic acid material used for most experiments was an 85 wt % aqueous solution of food-grade lactic acid (Purac, Inc., Lincolnshire, Ill.). The aqueous solution was diluted to 5 to 30% by weight which was then used in the reactions. In some experiments, calcium lactate or potassium lactate was used as the feedstock. These feedstocks were made by adding stoichiometric amounts of $Ca(OH)_2$ or KOH to the lactic acid material from Purac, Inc. which was then diluted to the appropriate concentration between 5 to 30% by weight.

The process used a stirred autoclave reactor (Model 4560, Parr Instrument Company, Moline, Ill.). The reactor was mounted in a bench top stand for conducting liquid-phase reactions. The reactor used for this example can withstand a maximum temperature of 350° C. and a maximum pressure of 20 MPa. The reactor was made of T316 stainless steel and the interior surfaces of the reactor was lined in quartz to further protect the reactor from corrosion. The reactor was equipped with a gas inlet valve for charging gas into the reactor, a gas release valve for releasing pressure, a dip tube connected to a liquid sampling valve for adding or withdrawing samples from the reactor when under pressure, a safety rupture disk for providing over pressure protection, a thermocouple for temperature measurements, and a stirring shaft with a gas entrainment impeller. The stirrer drive is a packless magnetic drive. The reactor is controlled by a Model 4852 controller (also from Parr Instrument Company), which provides adjustable stirring speeds, electric heater power, and automatic temperature control.

The liquid phase reactant and product concentrations were measured by high performance liquid chromatography (HPLC), and the gas phase products were quantified by mass spectrometry. The HPLC was a Spectra Tech P1000 (available from Thermo Separation Products, Fremont, Calif.) with both ultraviolet and refractive index detectors and the columns were Aminex HPX 87H ion exchange types (available from Bio-Rad, Inc., Richmond, Calif.). The mass spectrometer was a model M100M Quadrupole Residual Gas Analyzer (available from Ametek, Inc., Paoli, Pa.).

Liquid samples were withdrawn during the reaction and filtered using 0.2 µm syringe microfilters. Then the samples were mixed with an internal reference solution (1 wt % sucrose) and injected into the HPLC. Gas phase compositions were monitored continuously for mass numbers m/z= 1~50 with the mass spectrometer. Species concentrations were calculated by flowing calibration gases of known composition and comparing mass intensities for each gas sample.

Figure 3:
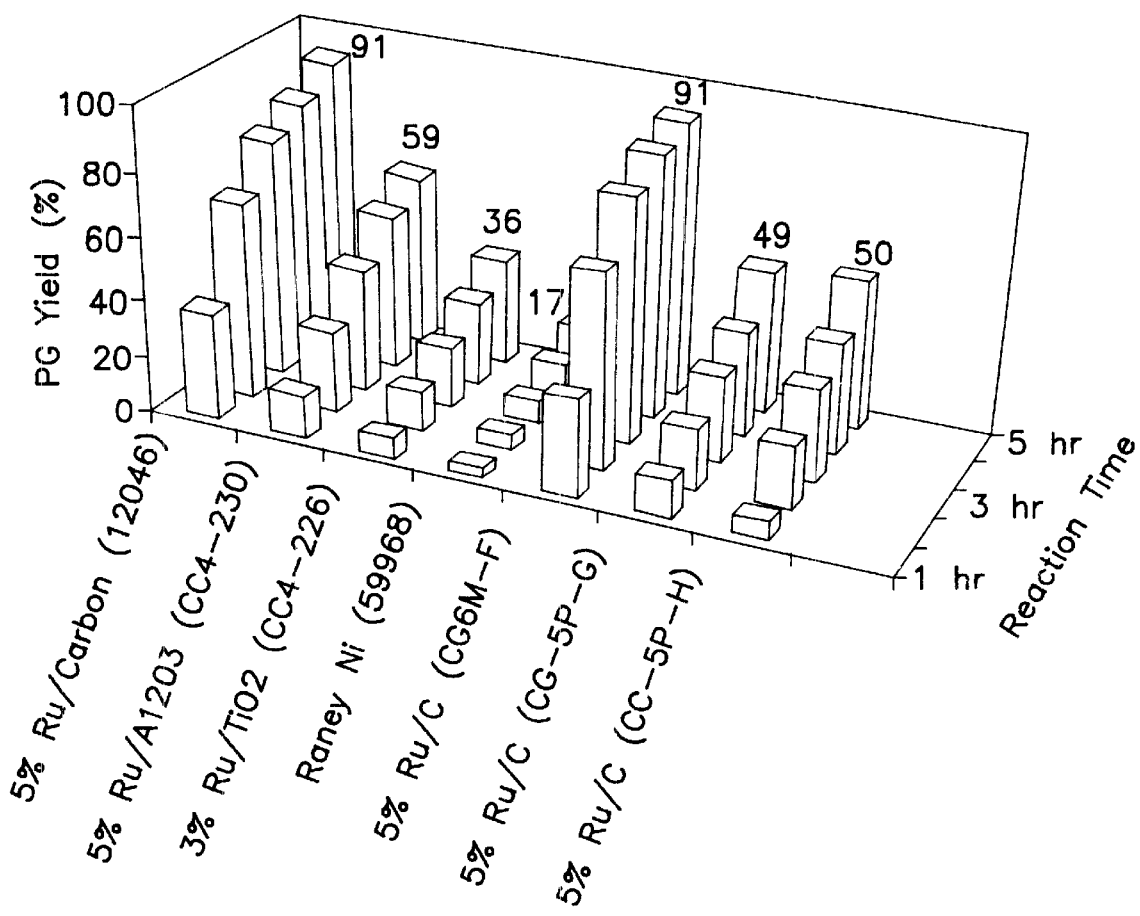
FIG. 3 is a bar chart that shows a comparison of propylene glycol (PG) yields as a function of reaction time for several prepared catalysts and commercial catalysts.

Propylene glycol yields as percent of theoretical yield for the catalysts are shown in FIG. 3 as a function of time for a reaction temperature of 150° C., 1.5 MPa, and 1% catalyst in solution. The results show that the 5% Ru/C (CG6M-F) catalyst was active for propylene glycol formation. The CG-5P-G and the CG5P-H catalysts produced one-half the yield of propylene glycol as the CG6M-F catalyst. However, the conversion rates for lactic acid to propylene glycol over the prepared ruthenium catalysts were more rapid than those of the prior art, and the reactions were performed under milder reaction conditions and at hydrogen pressures as low as 3.3 MPa.

Comparative Example

This example was performed to evaluate the efficacy in a batch reactor of commercially available catalysts that consisted of ruthenium catalysts on several supports and a Raney nickel catalyst.

The commercially available catalysts that were evaluated were a 5% Ruthenium on aluminum oxide (Ru/Al$_2$O$_3$; CC4-230 in FIG. 3; catalog No. H214 XR/W from Degussa Corp., Calvert City, Ky.); a 5% Ruthenium on carbon (Ru/carbon) with a dispersion of 34% (12046 in FIG. 3; catalog No. 1940C from precious Metals Corp., Sevierville, Tenn.); a 3% Ruthenium on titanium oxide (Ru/TiO$_2$) with a dispersion of 40% (CC4-226 in FIG. 3; catalog No. H7701 X/D from Degussa Corp.); and, a Raney Nickel (59968 in FIG. 3; catalog No. A-7063 from Activated Metals & Chemicals, Inc., Sevierville, Tenn.).

The results are shown in FIG. 3 and show that the 5% Ru/carbon catalyst (12046) gave results that were comparable to the prepared catalyst 5% Ru/C (CG6M-F) catalyst whereas the 5% Ru/Al2O3 (CC4-230) 3% Ru/TiO2 (CC4-226), and Raney Ni (59968) catalysts showed limited propylene glycol yield. Other catalysts such as palladium on a carbon support, nickel on alumina, and bulk copper chromite showed essentially no activity for propylene glycol formation from lactic acid (results not shown).

Figure 4:
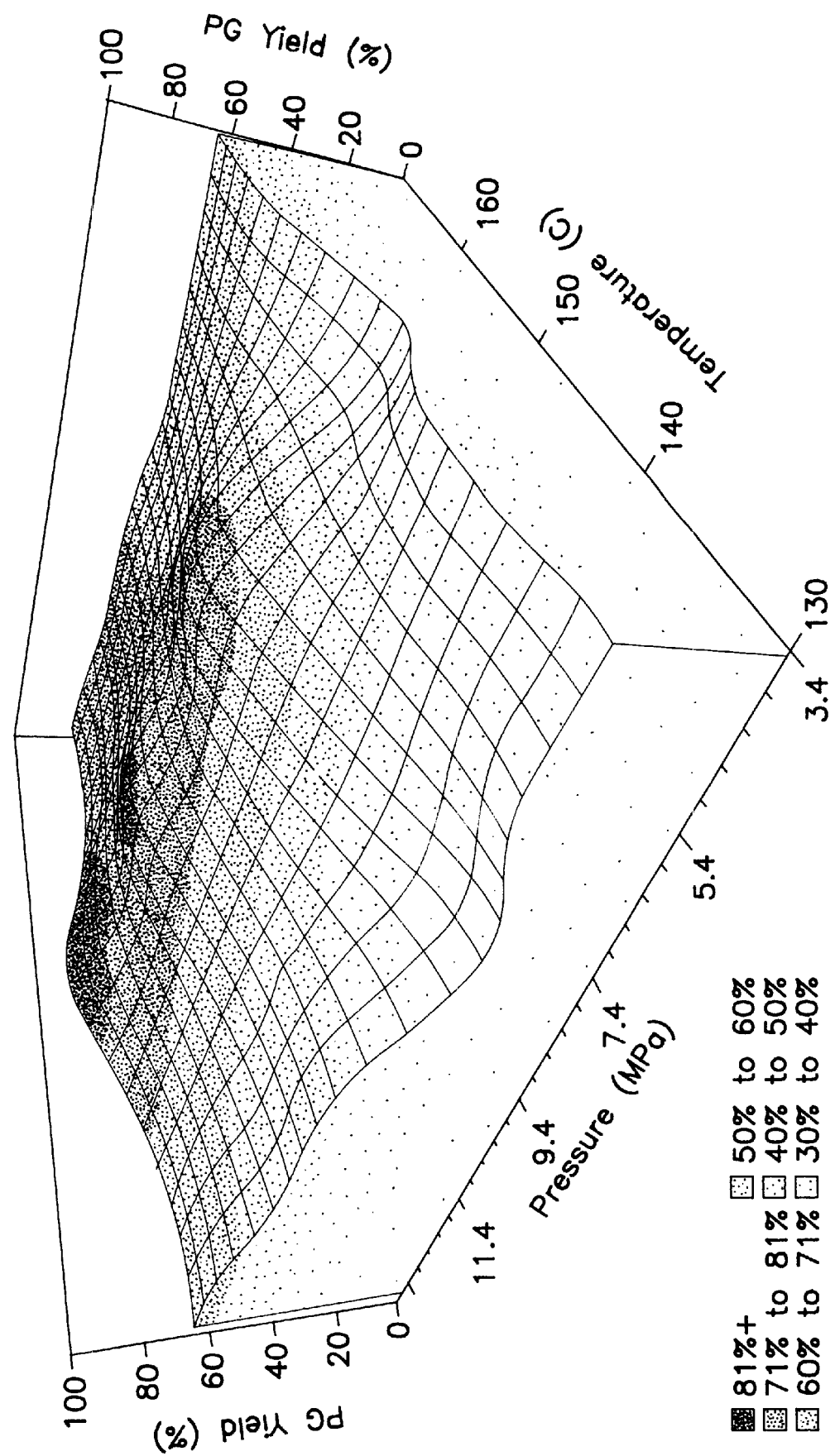
FIG. 4 is a three-dimensional graph that shows propylene glycol (PG) yield as a function of pressure and temperature.

FIG. 4 shows the propylene glycol yield after 5 hours in the reactor for commercial Ruthenium catalyst 1940C (12046 in FIG. 3) as a function of temperature from 130 to 170° C. and hydrogen pressure from 3.3 to 13.2 MPa. The results show that high hydrogen pressure and moderate temperature was most favorable for propylene glycol formation. By comparison, using the prepared CG6M-F catalyst, a maximum propylene glycol yield of 91% was obtained after 5 hours at a temperature of 150° C. and 13.5 MPa. The primary reaction by-product was methane. In a separate set of experiments, the rate of reactor stirring had no influence on the conversion of lactic acid to propylene glycol.

Figure 5:
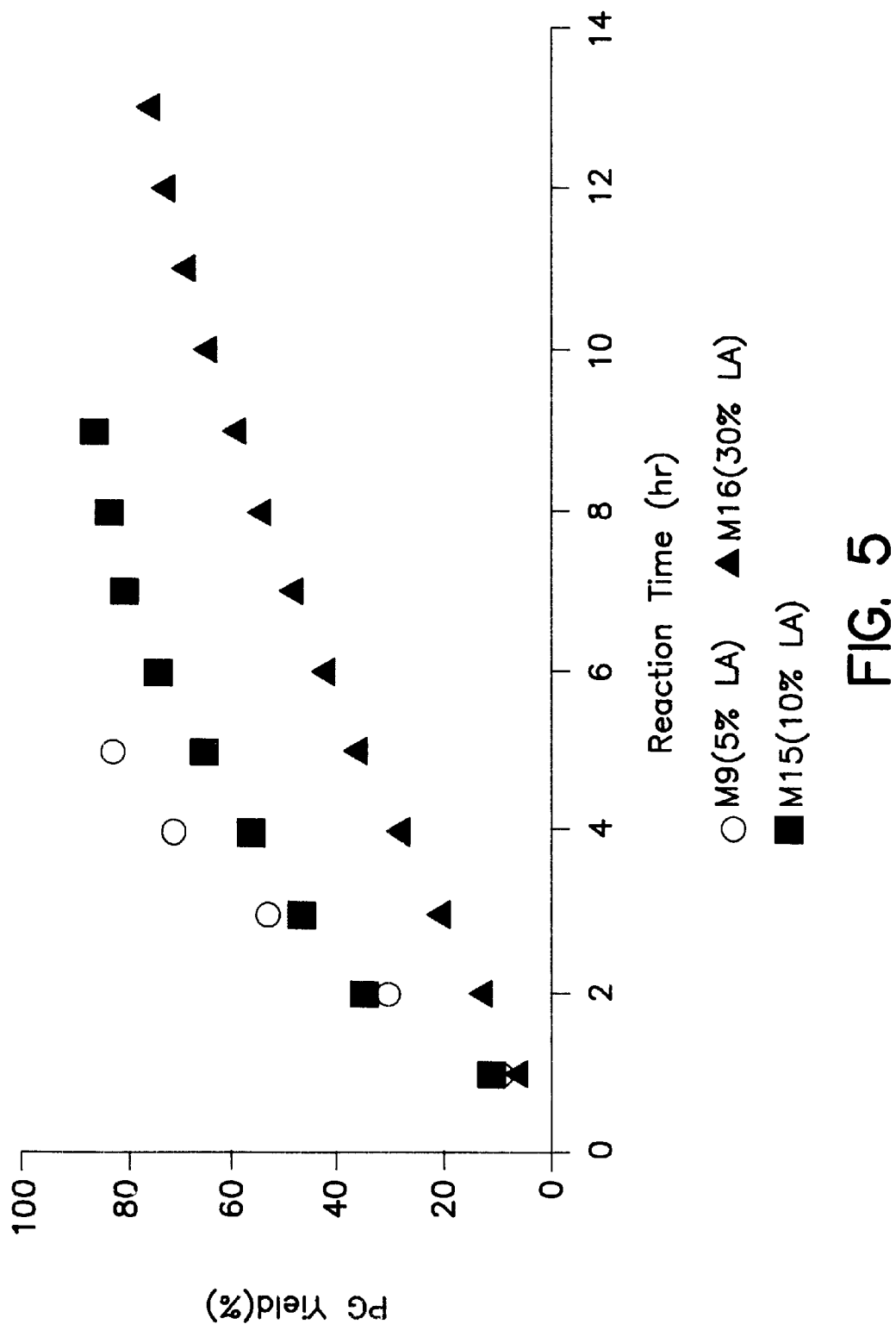
FIG. 5 is a graph that shows propylene glycol (PG) yield over time as a function of different initial lactic acid concentrations.

FIG. 5 shows the effect of initial lactic acid concentration in the feedstock over the range of 5% by weight in solution to 30% by weight in solution. The reactions shown in FIG. 5 were conducted with 5% Ruthenium catalyst (1940C) at 150° C. and 14.5 MPa hydrogen pressure at a loading of 1 gram catalyst per 100 grams solution. The fractional conversion rate was lower as the feedstock concentration was increased; however, the absolute rate of conversion increased as the lactic acid concentration was increased in the feedstock.

This example demonstrates that the process can effectively convert lactic acid to propylene glycol at different lactic acid concentrations.

EXAMPLE 3

This example shows an important advantage of the present invention which is the conversion of "unrefined" lactic acid to propylene glycol. Lactic acid made by a microorganism in a fermentor exits the fermentor as a salt, usually calcium lactate, and must be acidified prior to further use (usually by adding excess sulfuric acid).

Impure lactic acid is either a fermentate or lactic acid containing lactate salts. Impure lactic acid preferably contains 50 to 100% lactic acid.

In fermentation, lactic acid is produced as lactate salt, which may be partially acidified to produce a lactic acid and lactate salt mixture. This mixture can be treated by the process of the present invention which provides an economic source of lactic acid. Residual lactate can be further acidified and/or can be recycled into the crude broth. Lactate salt can be in the alkali metal, alkali earth, or ammonium lactate form as a fermentate. The lactic fermentate can be partially or fully acidulated.

Figure 6:
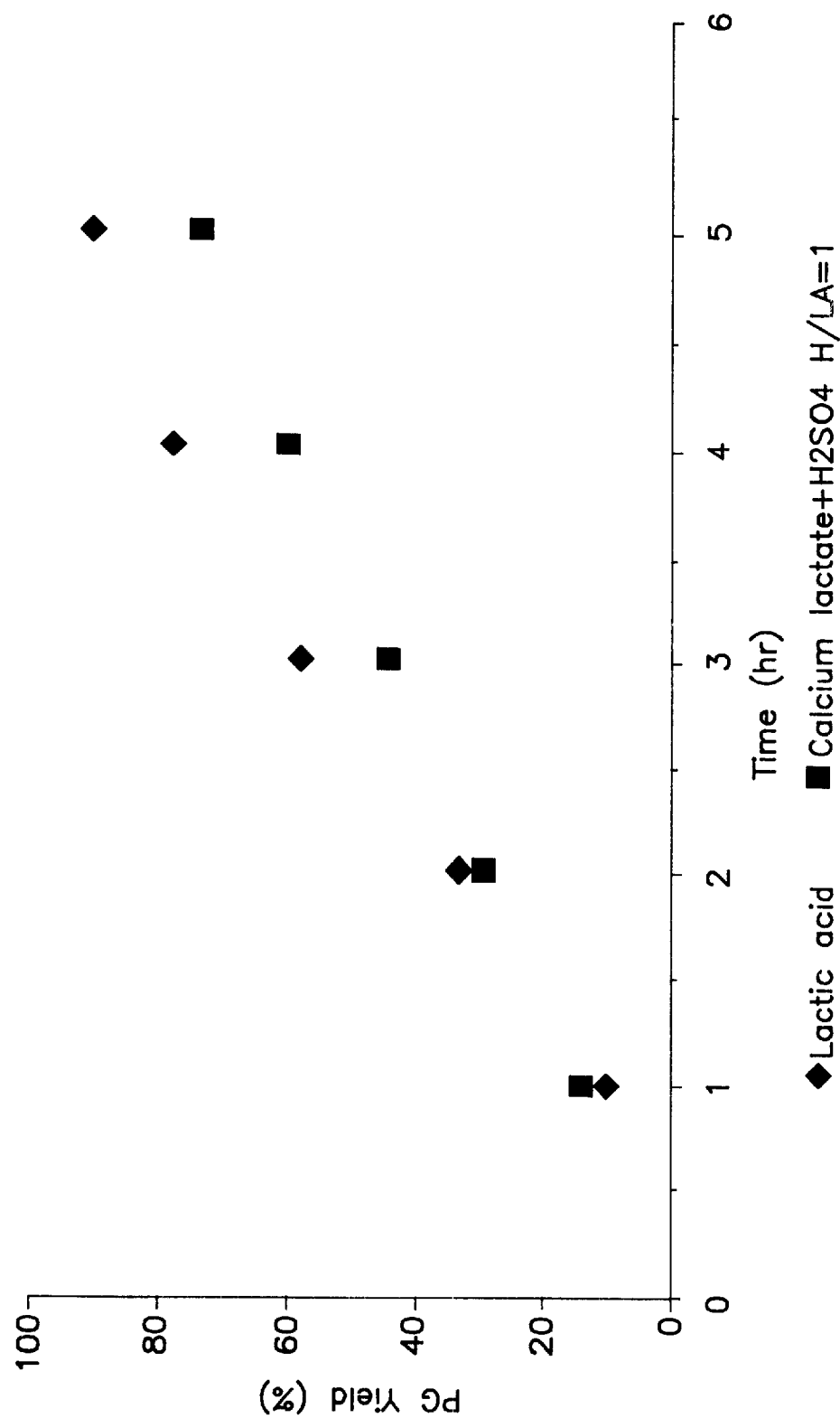
FIG. 6 is a graph that shows the results of a comparison of propylene glycol yields as a function of time between neat lactic acid and acidulated calcium lactate.

Hydrogenation reactions performed as in Example 2 showed that the conversion of calcium lactate or potassium lactate to propylene glycol was unsuccessful, and, in fact, the reaction was thermodynamically unfavorable. However, as shown in FIG. 6, when sulfuric acid was added to calcium lactate in a 1 to 1 molar ratio before performing the hydrogenation reaction, high yields of propylene glycol were obtained which were comparable to the conversion of neat lactic acid to propylene glycol. The reaction conditions were as in Example 2 at 150° C. and 14.5 MPa hydrogen pressure.

This result shows that the present invention enables the conversion of "unrefined" lactic acid to propylene glycol which is in contrast to the prior art wherein high purity lactic acid is to be the starting material.

EXAMPLE 4

This example shows the preferred method for preparing the catalysts of the present invention. These catalysts have the properties of the catalysts shown in Table 1.

The catalyst preparation method shown in Example 1 was used for the preparation of the additional catalysts except that the drying times and reduction conditions were slightly different. The newer, improved catalysts were dried at 25° C. for 5 hours and then under vacuum at 100° C. for 12 hours. The improved catalysts were then placed in a quartz tube reactor and heated from 25° C. to 400° C. at 0.5° C. per minute under a flow of 30 ml per minute of a gas consisting of 10 volume percent hydrogen and 90 volume percent helium. Once 400° C. was reached, the gas was switched to pure hydrogen and reduction was continued for 16 hours. The catalyst was then cooled under a helium flow to room temperature and passivated in a stream of 2% oxygen in argon for 1 hour. The support comprising the preferred catalysts are microporous and have a BET surface area between about 400 to 1,000 m$^2$ per gram. The preferred loading is 4 to 5 wt %.

A number of catalysts were prepared which had the properties of the catalysts shown in Table 1. These catalysts are preferred. These catalysts were evaluated for dispersion using hydrogen chemisorption in a flow cell system.

EXAMPLE 5

This example demonstrates the utility of the process of the present invention in a continuous trickle-bed reactor. This example shows the reaction mediated by catalysts CG5P-A and CG6M-F which were made according to the improved method in Example 4.

The reactor (inner diameter 0.62 inches and 18 inches in length) which was jacketed and temperature controlled with a temperature controller from Omega Engineering, Stanford, Connecticut was charged with 50 to 75 ml of catalyst. The feed gas rate to the reactor was controlled by mass flow controllers and the feed hydrogen was passed through water saturators prior to entering the reaction to avoid flashing of the liquid feed in the reactor. The liquid feedstock solution was fed via an HPLC pump (available from Bio-Rad, Inc.). The reactor effluent was passed through a cold-water condenser and into a phase separator wherein the liquid product was allowed to settle out. The gas effluent was passed through a back pressure regulator and to the exhaust. A portion of the gas effluent was drawn into a mass spectrometer wherein the effluent gas composition was determined.

The reactions were carried out at a temperature from about 80° to 150° C. and at pressures ranging from about 3.4 to 8.3 MPa (500 to 1,200 PSIG). Lactic acid was fed to the reactor in aqueous solutions of 5 to 20% by weight. The liquid feed rate to the reactor ranged from 0.5 to 3.0 ml per minute, which gave a weight hourly space velocity (kg lactic acid/kg catalyst/hour) of 0.3 to 2.0. The hydrogen to lactic acid feed molar ratio ranged from 2:1 to 10:1.

To perform the trickle-bed reaction, the catalyst was first loaded into the reactor and then reduced at the reaction temperature for 1 hour to remove the passivating oxide layer. Once the catalyst had been reduced, water was fed to the reactor while the temperature was brought to the desired steady-state condition. The liquid was then switched to the lactic acid containing feedstock solution and the hydrogen pressure was increased to the desired value. It generally took about 90 to 120 minutes for the steady-state product compositions to be achieved at any particular set of conditions. Thus, several different reaction conditions could be evaluated over the course of a day.

A summary of several reactions conducted in a trickle-bed reactor over two different ruthenium over carbon (Ru/C) catalysts is shown in Table 2. These catalysts were CG6M-F and CG5P-A with the properties for these catalysts shown in Table 1. In these reactions, the feedstock was 10 wt % lactic acid in water at a flow rate of 1.0 ml per minute. The quantity of catalyst in the bed was 27–30 grams and the hydrogen pressure was 8.3 MPa (1,200 PSIG). The temperature ranged from 80° C. to 120° C. The results in Table 2 clearly demonstrate that the process of the present invention is efficient when performed in a continuous mode of operation. In particular, the present invention shows that the CG6M catalyst is preferred over the CG5P catalyst. Reactions n9 and n10 which were both run at 120° C., showed that the CG6M catalyst had a selectivity of 86% with a conversion of over 95%.

In contrast, the CG5P catalyst under the same conditions had a selectivity of about 82% with a conversion of about 95%. Table 2 further shows that the process of the present invention can be performed over a temperature range between 100° C. and 140° C. and still produce yields of propylene glycol greater than 70% when using the CG6M catalyst and between 120° C. and 140° C. to achieve similar with the CG5P catalyst.

TABLE 2

|  | Temp (° C.) | $H_2$:lactic Ratio | Lactic Conv. % | PG Yield % | PG Selectivity % | Yield $CH_4$ (% of LA) | Yield $C_2H_6$ (% of LA) | Carbon Balanace % recov. | exp. |
|---|---|---|---|---|---|---|---|---|---|
| Catalyst CG6M | 80 | 3.4 | 35% | 27% | 77% | 0.1% | 9.1% | 101.3% | n1 |
|  | 100 | 3.4 | 67% | 58% | 87% | 0.0% | 10.5% | 101.5% | n7 |
|  | 120 | 3.4 | 82% | 72% | 88% | 0.8% | 4.5% | 95.1% | n8 |
|  | 80 | 5.7 | 31% | 24% | 77% | 0.9% | 7.3% | 101.3% | n2 |
|  | 100 | 5.7 | 66% | 58% | 88% | 0.7% | 6.2% | 98.9% | n6 |
|  | 120 | 5.7 | 95% | 82% | 86% | 3.0% | 5.5% | 95.5% | n9 |
|  | 80 | 9.5 | 36% | 29% | 81% | 0.2% | 6.6% | 99.9% | n4 |
|  | 100 | 9.5 | 62% | 56% | 90% | 0.9% | 7.1% | 102.0% | n5 |
|  | 120 | 9.5 | 98% | 84% | 86% | 4.0% | 11.3% | 101.3% | n10 |
| Catalyst CG5P | 80 | 2.5 | 25% | 20% | 80% | 1.1% | 6.3% | 102.4% | 13-n2 |
|  | 100 | 2.5 | 50% | 43% | 86% | 4.3% | 3.3% | 100.6% | 14-n1 |
|  | 120 | 2.5 | 67% | 57% | 85% | 5.4% | 3.9% | 99.2% | 14-n2 |
|  | 80 | 5 | 23% | 18% | 78% | 0.4% | 2.8% | 98.3% | 13-n3 |
|  | 100 | 5 | 54% | 46% | 85% | 1.7% | 7.1% | 100.8% | 13-n7 |
|  | 120 | 5 | 90% | 74% | 82% | 10.1% | 8.2% | 102.2% | 14-n3 |
|  | 130 | 5 | 93% | 72% | 77% | 14.4% | 7.7% | 101.1% | 14-n6 |
|  | 140 | 5 | 97% | 72% | 74% | 10.8% | 15.6% | 101.4% | 14-n5 |
|  | 80 | 7.5 | 22% | 17% | 77% | 0.6% | 3.6% | 99.2% | 13-n4 |
|  | 100 | 7.5 | 64% | 48% | 75% | 1.4% | 7.5% | 92.8% | 13-n6 |
|  | 120 | 6 | 95% | 79% | 83% | 11.6% | 6.0% | 101.6% | 14-n4 |

EXAMPLE 6

This example shows the effect of changing the flow rate of the feedstock solution in a trickle-bed reactor. The reactions were performed using catalyst CG5P as in Example 5 except that the temperature was 100° C., the hydrogen pressure was 8.3 MPa (1,200 PSIG), and the hydrogen to lactic acid molar ratio was 4:1.

Figure 7:
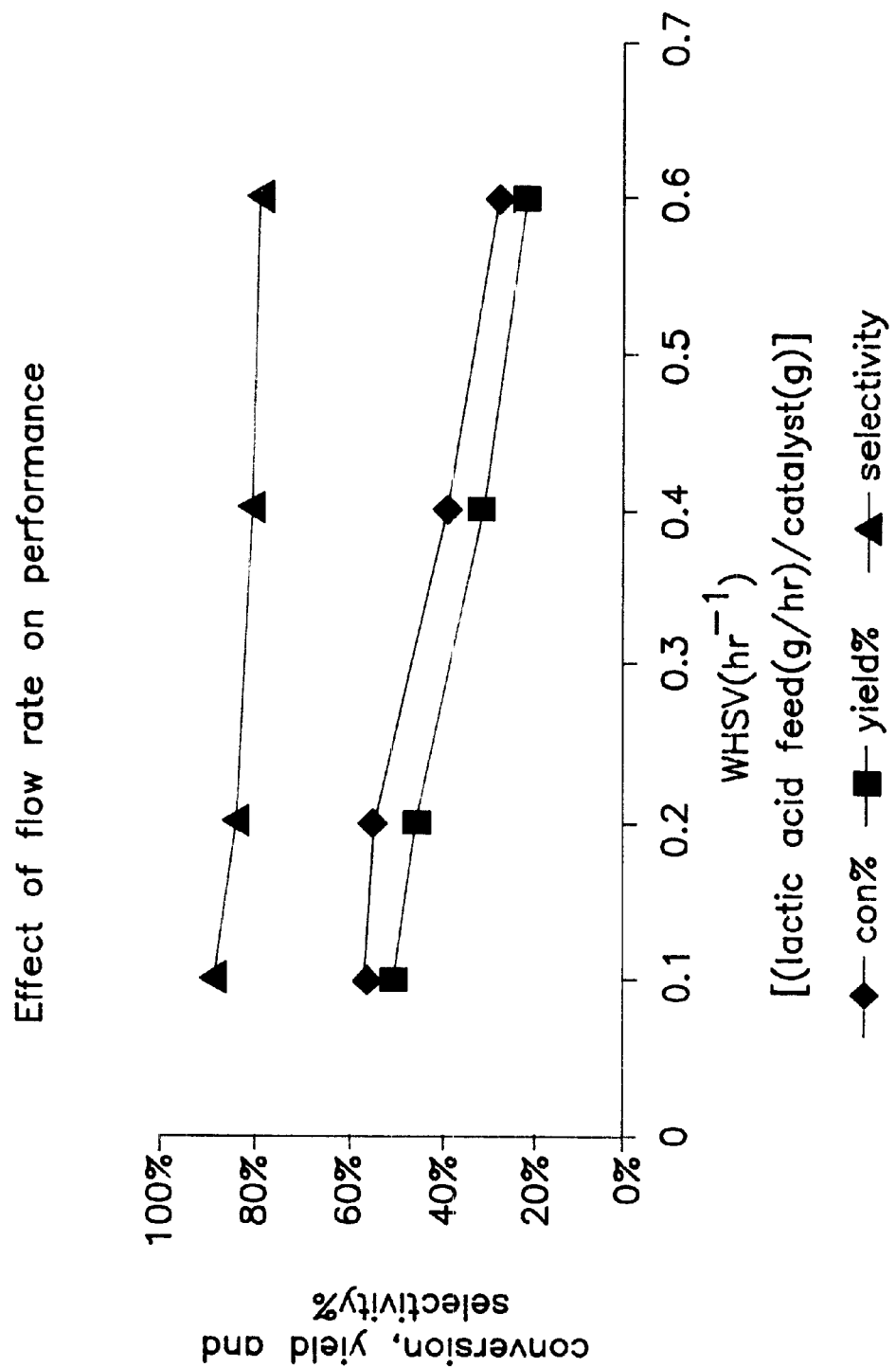
FIG. 7 is a graph that shows the effect of liquid feedstock flow rate on catalyst performance. The graph measures the percent lactic acid conversion (con %), percent propylene glycol yield (yield %) and selectivity at various lactic acid feedstock flow rates (WHSV).

FIG. 7 shows the effect of changing the liquid flow rate in the continuous trickle-bed reactor containing the CG5P catalyst. The reaction conditions were 100° C., 8.3 MPa (1,200 PSIG) hydrogen, and a 4 to 1 molar ratio of hydrogen to lactic acid. The feed concentration of lactic acid was 10 wt % in water. FIG. 7 shows that as the flow rate is increased there is a concomitant decrease in both conversion and selectivity at the above chosen conditions. Reactions conducted at 5.5 and 6.9 MPA (800 and 1,000 PSIG) hydrogen pressure were also performed which gave slightly lower but acceptable conversion of lactic acid to propylene glycol and lower selectivity to propylene glycol. Reactions were not performed at pressures greater than 8.3 MPa (1,200 PSIG)

hydrogen; however, it is expected that higher pressures would further improve selectivity to propylene glycol yield.

Thus, when the reactions were performed at a hydrogen pressure of 8.3 MPa (1,200 PSIG), increasing the flow rate resulted in a decrease in both conversion and selectivity. Additional reactions were conducted at 5.5 to 6.9 MPa (800 to 1,000 PSIG) hydrogen pressure. In these reactions, there was a slightly lowerconversion of lactic acid and lower selectivity to propylene glycol (data not shown).

TABLE 3

Trickle Bed reactor Performance At Elevated feed Concentrations

| Latic acid feed Conc. (wt %) | WHSV (hr$^{-1}$) | Lactic acid conversion | Propylene glycol yield | Selectivity to Propylene glycol | CH$_4$ yield | C$_2$H$_4$ yield | Carbon balance (% recovery) |
|---|---|---|---|---|---|---|---|
| 10 | 0.22 | 54% | 46% | 85% | 1.7% | 7.1% | 100.8 |
| 17.2 | 0.37 | 45% | 34% | 76% | 3.0% | 9.0% | 99.0 |

EXAMPLE 7

This example shows the efficacy of the CG5P catalyst in the conversion of lactic acid to propylene glycol at a feed concentration of 17.2 wt % compared to the catalyst's efficacy at a feed concentration of 10 wt %.

The reactions were performed in a trickle-bed reactor using the conditions similar to those shown in Example 5 with the following noted. The reaction temperature was 100° C., the hydrogen pressure was 8.3 MPa (1,200 PSIG), and the H$_2$ to lactic acid ratio was 5 to 1. The results are shown in Table 3. It is noteworthy that these two reactions in Table 3, while conducted at the same overall flow rate, have different space velocities because of the higher lactic acid concentration. The drop off in selectivity in going to the higher concentration corresponds to the decrease in selectivity A in going to a higher flow rate, as seen in FIG. 7. Thus, at the same WHSV, the higher feed concentration gives the same performance.

EXAMPLE 8

This example compares the efficacy of the catalysts having the properties of the catalysts shown in Table 1 in the conversion of lactic acid to propylene glycol in a batch reactor.

The reactions were performed as in Example 2 but with the following conditions. The temperature was 150° C. and the pressure was 14.2 MPa (2,100 PSIG). The initial feedstock solution was 100 grams which contained 5 grams of lactic acid, and 1 gram of catalyst. The catalysts were those shown in Table 1. The results shown in FIG. 8 were from measurements taken after a reaction time of 5 hours.

Figure 8:
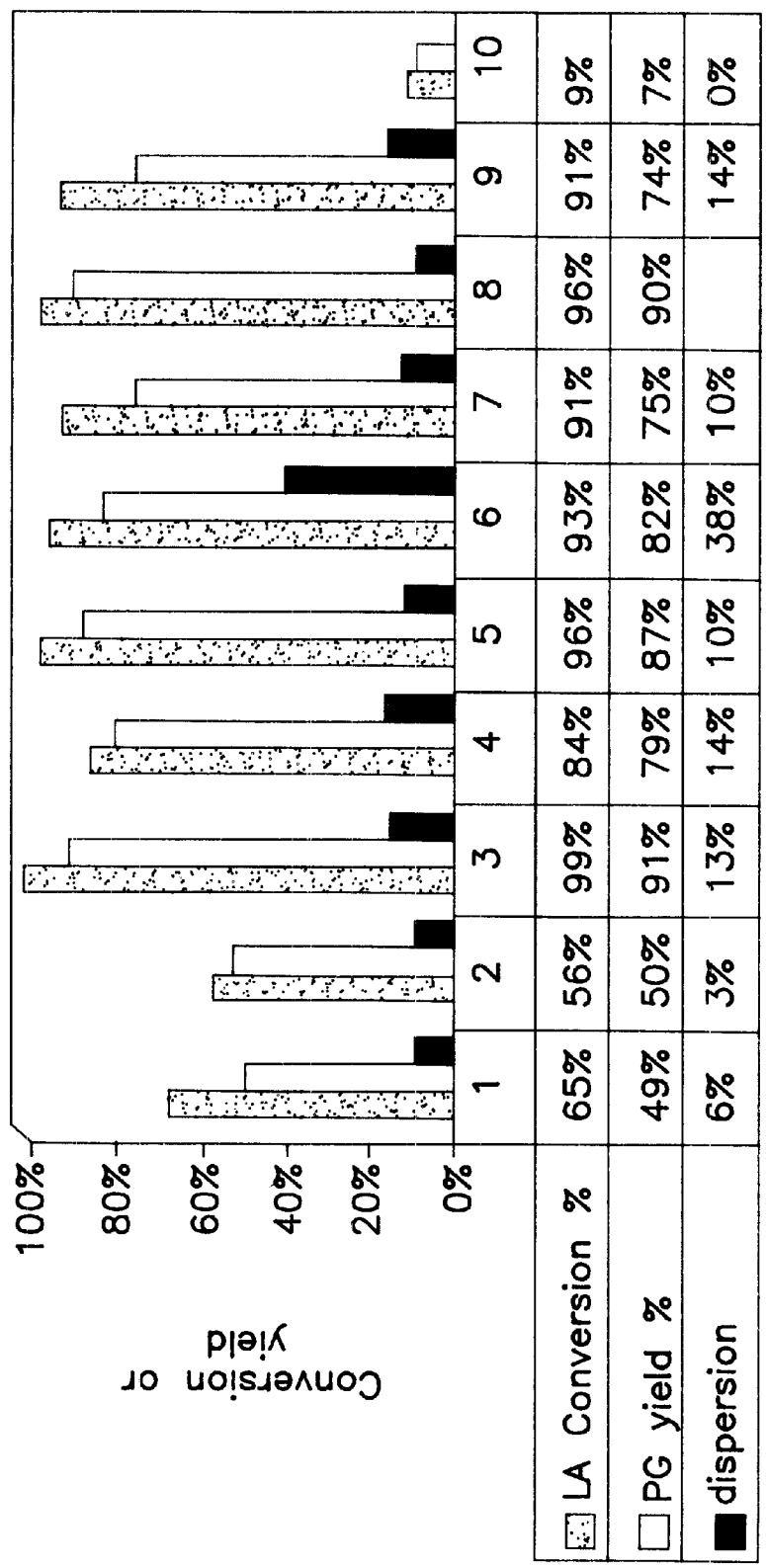
FIG. 8 is a bar graph that shows the percent lactic acid (LA) conversion, percent propylene glycol (PG) yield, and percent dispersion for catalysts 1 through 10 which have the properties of catalysts 1 through 10 shown in Table 1.

FIG. 8 shows that the CG6M-F, SG6-D, and TiP25-C19-J catalysts (runs 3, 5, and 8 of Table 1, respectively) gave propylene glycol yields 87% or greater with selectivities 96% or greater. Clearly these catalysts are preferred. Catalysts CG5P-NO1-I, CG5P-A, and ALg-E (runs 6, 7, and 9 of Table 1, respectively) were effective as well, but not as effective as the preferred catalysts. Thus, catalysts 3 through 9 were very effective in the conversion of lactic acid to propylene glycol with high selectivity. As expected, the efficacy of catalyst 10 was substantially less. In all the reactions, some lactic acid was converted to the gaseous products methane and ethane. However, the overall carbon material balance in the reactions closed to within ±4%, which indicated that the reaction results were reliable.

EXAMPLE 9

This example shows the preparation of preferred catalyst CG6M-F.

CG6M-F was made according to the method shown in Example 4. The support was a 110+200 mesh particle size carbon support with a BET surface area of 728 m$^2$ per gram (available from Cameron-Yakima, Inc.). The ruthenium metal loading was 5.0 wt % which was applied to the support as an aqueous solution of ruthenium chloride hydrate with a dispersion of 13%. This catalyst is shown as run 3 in Table 1.

EXAMPLE 10

This example shows the preparation of preferred catalyst SG6-D.

Catalyst SG6-D was made according to the method in Example 4. The support was a 100 mesh microporous carbon support with a BET surface area of 777 m$^2$ per gram (available from Cameron-Yakima, Inc.). The ruthenium metal loading was 4.4 wt % which was applied as an aqueous solution of ruthenium chloride hydrate with a dispersion of 10%. This catalyst is shown as run 5 in Table 1.

EXAMPLE 11

This example shows the preparation of preferred catalyst CG5P-NO1-I.

Catalyst CG5P-NO1-I was made according to the method in Example 4. The support was a microporous CG5P-200 mesh carbon support with a BET surface area of 648 m$^2$ per gram (available from Cameron-Yakima, Inc.). The ruthenium metal loading was 5.0 wt % which was applied as an aqueous solution of ruthenium nitrosyl nitrate hydrate with a dispersion of 38%. This catalyst is shown as run 6 in Table 1.

EXAMPLE 12

This example shows the preparation of preferred catalyst CG5P-A.

Catalyst CG5P-A was made according to the method in Example 4. The support was a microporous CG5P 20*50 mesh carbon support with a BET surface area of 648 m$^2$ per gram (available from Cameron-Yakima, Inc.). The ruthenium metal loading was 5.4 wt % which was applied as an aqueous solution of ruthenium chloride hydrate with a dispersion of 10%. This catalyst is shown as run 7 in Table 1.

EXAMPLE 13

This example shows the preparation of preferred catalyst SA135-C.

Catalyst SA135-C was made according to the method in Example 4. The support was a silica-alumina grade 135, −100 mesh support with a BET surface area of 440 m² per gram (available from Aldrich Chemical Company). The ruthenium metal loading was 5 wt % which was applied to the support as an aqueous solution of ruthenium chloride hydrate with a dispersion of 14%. This catalyst is shown as run 4 in Table 1.

EXAMPLE 14

This example shows the preparation of preferred catalyst TiP25-C19-J.

Catalyst TiP25-C19-J was made according to the method in Example 4. The support was a titania 200 mesh support with a BET surface area of 49 m² per gram (available from Degussa Corporation). The ruthenium metal loading was 5 wt % which was applied to the support as an aqueous solution of ruthenium chloride hydrate. This catalyst is shown as run 8 in Table 1.

EXAMPLE 15

This example shows the preparation of preferred catalyst ALg-E.

Catalyst ALg-E was made according to the method in Example 4. The support was a gamma aluminum oxide +200 mesh support with a BET surface area of 45 m² per gram (available from Johnson Matthey Chemicals, Inc.). The ruthenium metal loading was 4.7 wt % which was applied to the support as an aqueous solution of ruthenium chloride hydrate with a dispersion of 13.5%. This catalyst is shown as run 9 in Table 1.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for the production of propylene glycol, which comprises:
    (a) providing an oxide passivated ruthenium catalyst in a closed reaction vessel;
    (b) activating the passivated catalyst by removing the oxide with hydrogen;
    (c) reacting a reaction mixture of lactic acid in water and hydrogen with the activated ruthenium catalyst on an inert support with a BET surface area between about 1 to 1,000 m² per gram at a hydrogen pressure between about 3.4 to 16.5 MPa and a temperature between about 50° to 200° C.; and
    (d) recovering the propylene glycol from the reaction mixture.

2. The process of claim 1 wherein the concentration of the lactic acid in step (c) is between about 5% and 50% by weight of the reaction mixture.

3. The process of claim 1 wherein the hydrogen pressure in step (c) is between about 3.4 to 8.3 MPa.

4. The process of claim 1 or 2 wherein the temperature in step (c) is between about 70° to 150° C.

5. The process of claim 1 as a batch process wherein the reaction mixture is in the closed reaction vessel provided with a stirrer which agitates the reaction mixture.

6. The process of claim 1 as a continuous process wherein the reaction mixture is trickled through a bed of the activated ruthenium catalyst in step (c).

7. The process of claim 1 wherein the inert support is selected from the group consisting of alumina, titania, silica, aluminosilicate, and microporous carbon.

8. The process of claim 1 as a continuous process wherein the reaction mixture in step (c) has a space velocity of between about 0.5 and 5 grams of the lactic acid per gram of catalyst per hour.

9. The process of claim 1 as a batch process in the closed reaction vessel provided with stirrer which agitates the reaction mixture in step (c) for between 2 to 12 hours prior to recovering the propylene glycol.

10. The process of claim 1 wherein the lactic acid is present in an impure form in an aqueous fermentate produced by a microorganism.

11. The process of claim 1 wherein the reaction mixture contains sulfur.

12. The process of claim 1 wherein the propylene glycol is recovered in a yield of at least 80% and a selectivity to propylene glycol of at least 80%.

13. A process for preparation of propylene glycol comprises:
    (a) providing an oxide coated ruthenium metal catalyst prepared by (i) reacting hydrogen-containing gas with a ruthenium salt deposited and dried on an inert microporous support having a BET surface area between about 1 and 1,000 m² per gram; and
        (ii) drying the catalyst in an oxygen containing atmosphere so as to provide oxide of the ruthenium on surfaces of the ruthenium;
    (b) introducing the dried catalyst into a closed reaction vessel;
    (c) reacting the catalyst with the oxide on the surface with hydrogen in the closed reaction vessel;
    (d) reacting in the closed reaction vessel at elevated pressures and at elevated temperatures, a reaction mixture of lactic acid in water in the presence of the catalyst, wherein the temperature is between about 70° to 170° C. and the hydrogen pressure is between about 3.4 to 16.5 MPa to produce the propylene glycol in the reaction mixture; and
    (e) recovering the propylene glycol from the reaction mixture.

14. The process of claim 13 wherein the lactic acid is provided in impure form as a fermentate produced by a microorganism.

15. The process of claim 13 or 14 wherein the lactic acid is provided in an impure form as its salt or a partially acidulated salt and the reaction mixture further comprises an added acid other than lactic acid.

16. The process of claim 15 wherein the acid is $H_2SO_4$.

17. The process of claim 16 wherein the $H_2SO_4$ is added to provide a molar ratio of lactate salt to acid equivalent of one to one.

18. The process of claim 14 wherein the lactic acid is provided at a concentration between about 5% and 50% by weight of the reaction mixture.

19. The proceed of claim 13 wherein the hydrogen pressure in step (d) is between about 3.4 to 8.3 MPa.

20. The process of claim 13 wherein the temperature in step (d) is between about 50° C. to 200° C.

21. The process claim 13 wherein the support is selected from the group consisting of alumina, titania, silica, aluminosilicate, and microporous carbon.

22. The process of claim 13 as a batch process wherein the reaction mixture is in the closed reaction vessel provided with a stirrer which agitates the reaction mixture.

23. The process of claim 13 as a continuous process wherein the reaction mixture is trickled through a bed of the catalyst.

24. The process of claim 13 as a continuous process wherein the reaction mixture has a space velocity of between about 0.5 and 5 grams of the lactic acid per gram of the catalyst per hour.

25. The process of claim 13 wherein the reaction mixture further contains sulfur.

26. The process of either claim 1 or 13 wherein the propylene glycol is recovered in a yield of at least 80% and a selectivity to propylene glycol of at least 80%.

27. The process of claim 1 wherein the passivated catalyst is prepared by depositing an essentially pure elemental ruthenium on an inert microporous support, wherein the ruthenium is deposited on the support by drying a water solution of ruthenium salt on the support, reducing the salt to elemental ruthenium on the support with hydrogen, and then passivating the composition in an oxygen containing atmosphere so as to provide an oxide of the ruthenium on surfaces of the ruthenium.

28. The process of claim 27 wherein drying the ruthenium salt on the catalyst is at about 25° C. for about 5 hours and then under a vacuum of about 30 inches of mercury at about 100° C. for 12 hours.

29. The process of claim 27 wherein reducing the ruthenium salt to elemental ruthenium comprises the steps of (a) heating the catalyst from 25° C. to 400° C. at a rate of about 0.5° C. per minute under a flow of a gas consisting of 10 volume percent of hydrogen in helium at a rate of about 30 ml per minute;

(b) maintaining the catalyst at 400° C. and changing the gas to pure hydrogen;

(c) reducing the catalyst in the pure hydrogen for about 16 hours; and (d) cooling the catalyst under a helium flow to room temperature.

30. The process of claim 27 wherein passivating the catalyst comprises placing the reduced catalyst in a stream of about between 1 to 10 volume percent of oxygen in an inert gas at room temperature for about 1 hour.

31. The process of claim 27 wherein the inert gas is between about 1 to 3 volume percent.

32. A continuous process for the production of propylene glycol, which comprises:

(a) reacting a reaction mixture of lactic acid in water and a molar excess of hydrogen with a ruthenium catalyst on an inert support with a BET surface area between about 1 to 1,000 $m^2$ per gram at a hydrogen pressure between about 3.4 to 16.5 Mpa and a temperature between about 50° to 200° C.;

(b) recovering the propylene glycol from the reaction mixture along with unreacted hydrogen;

(c) separating the unreacted hydrogen from the reaction mixture and purifying the hydrogen with the removal of methane; and (d) recycling the purified hydrogen to the reaction mixture.

33. The process of claim 32 wherein the concentration of lactic acid is between about 5% and 50% by weight of the reaction mixture.

34. The process of claim 32 wherein the hydrogen pressure is between about 3.4 to 8.3 MPa.

35. The process of claim 32 wherein the temperature is between about 70° to 150° C.

36. The process of claim 32 wherein the reaction mixture is trickled through a bed of the catalyst.

37. The process of claim 32 wherein the ruthenium is supported on an inert substrate.

38. The process of claim 32 wherein the inert support is selected from the group consisting of alumina, titania, silica, aluminosilicate, and microporous carbon.

39. The process of claim 32 wherein the reaction mixture has a space velocity of between about 0.5 and 5 grams of the lactic acid per gram of the catalyst per hour.

40. The process of claim 32 wherein the lactic acid is present in an aqueous fermentate produced by a microorganism.

41. The process of claim 32 wherein the reaction mixture contains sulfur.

42. The process of claim 32 wherein the propylene glycol is recovered in a yield of at least 80% and a selectivity to propylene glycol of at least 80%.

* * * * *

UNITED STATES PATENT AND TRADEMARK OFFICE
CERTIFICATE OF CORRECTION

PATENT NO. : 6,403,765 B1
DATED : June 11, 2002
INVENTOR(S) : Emad S. Alnemri

It is certified that error appears in the above-identified patent and that said Letters Patent is hereby corrected as shown below:

<u>Title page,</u>
Item [75], Inventors, "Emad S. Alnemri, Township Upper Dublin, County Montgomery, PA (US)" should read -- Emad S. Alnemri, Ambler, PA (US) --.

Signed and Sealed this

Twenty-eighth Day of January, 2003

JAMES E. ROGAN
*Director of the United States Patent and Trademark Office*